United States Patent
Luo et al.

(10) Patent No.: US 12,207,952 B2
(45) Date of Patent: Jan. 28, 2025

(54) EVALUATION SYSTEM BASED ON ANALYTE DATA

(71) Applicant: SHENZHEN SIBIONICS TECHNOLOGY CO., LTD., Shenzhen (CN)

(72) Inventors: Pei Luo, Shenzhen (CN); Can Peng, Shenzhen (CN); Shishan Liu, Shenzhen (CN); Xiaohui Xiong, Shenzhen (CN); Jian Li, Shenzhen (CN); Shixin Zhan, Shenzhen (CN); Zhongzhao Chen, Shenzhen (CN); Mingsong Han, Shenzhen (CN); Qiang Hao, Shenzhen (CN)

(73) Assignee: SHENZHEN SIBIONICS TECHNOLOGY CO., LTD., Shenzhen (CN)

( * ) Notice: Subject to any disclaimer, the term of this patent is extended or adjusted under 35 U.S.C. 154(b) by 209 days.

(21) Appl. No.: 18/145,077

(22) Filed: Dec. 22, 2022

(65) Prior Publication Data

US 2023/0129975 A1     Apr. 27, 2023

Related U.S. Application Data

(63) Continuation of application No. PCT/CN2021/133303, filed on Nov. 25, 2021.

(30) Foreign Application Priority Data

Aug. 27, 2021   (CN) .......................... 202110998641.0

(51) Int. Cl.
*A61B 5/00* (2006.01)
*G06V 10/20* (2022.01)
(Continued)

(52) U.S. Cl.
CPC ............ *A61B 5/742* (2013.01); *A61B 5/7275* (2013.01); *G06V 10/255* (2022.01);
(Continued)

(58) Field of Classification Search
CPC ...... A61B 5/742; A61B 5/7275; G16H 10/40; G16H 50/30; G06V 20/695; G06V 10/255; G06V 2201/02
See application file for complete search history.

(56) References Cited

U.S. PATENT DOCUMENTS

| 6,687,546 B2 * | 2/2004 | Lebel ..................... G16H 20/17 |
| | | 128/903 |
| 7,344,500 B2 * | 3/2008 | Talbot .................. A61B 5/0002 |
| | | 600/365 |

(Continued)

FOREIGN PATENT DOCUMENTS

| CN | 103561634 A | 2/2014 |
| CN | 109475296 A | 3/2019 |

OTHER PUBLICATIONS

Ledesma, 2016, BMC Medical Informatics and Decision Making, pp. 1-19.*

*Primary Examiner* — Michael I Ezewoko
(74) *Attorney, Agent, or Firm* — AVEK IP, LLC

(57) ABSTRACT

Some embodiments of the disclosure describe an evaluation system based on analyte data including a memory storing a program, a display, and a processor. In some examples, the processor is configured to: receive analyte data during a predetermined time period from an object to be tested, acquire a plurality of analyte indicators different from each other based on the analyte data, normalize the plurality of analyte indicators to a predetermined range to acquire a plurality of normalized analyte indicators, plot a polygon pattern corresponding to the analyte data during the first time period as a target polygon pattern, plot a polygon
(Continued)

pattern corresponding to the analyte data during the second time period as a reference polygon pattern, and take a line segment between a vertex and a center point as an axis, and display the target polygon pattern and the reference polygon pattern.

17 Claims, 4 Drawing Sheets

(51) Int. Cl.
    *G06V 20/69*     (2022.01)
    *G16H 10/40*     (2018.01)
    *G16H 50/30*     (2018.01)

(52) U.S. Cl.
    CPC ........... *G06V 20/695* (2022.01); *G16H 10/40* (2018.01); *G16H 50/30* (2018.01); *G06V 2201/02* (2022.01)

(56) References Cited

U.S. PATENT DOCUMENTS

| | | | | |
|---|---|---|---|---|
| 7,811,231 B2 * | 10/2010 | Jin | ............................ | A61B 5/01 600/300 |
| 8,187,183 B2 * | 5/2012 | Jin | ........................ | A61B 5/0002 600/301 |
| 8,542,122 B2 * | 9/2013 | Goodnow | ............. | A61B 5/7275 600/347 |
| 8,617,069 B2 * | 12/2013 | Bernstein | ............... | A61B 5/002 600/347 |
| 8,622,903 B2 * | 1/2014 | Jin | ............................ | A61B 5/01 600/301 |
| 8,672,844 B2 * | 3/2014 | Say | ....................... | H01L 23/3107 600/365 |
| 9,035,767 B2 * | 5/2015 | Fennell | ............... | A61B 5/14865 340/539.22 |
| 9,226,701 B2 * | 1/2016 | Sloan | ....................... | A61B 5/14 |
| 9,310,230 B2 * | 4/2016 | Harper | ............... | A61B 5/14532 |
| 9,846,887 B1 * | 12/2017 | Cranshaw | .......... | G06Q 30/0205 |
| 9,904,932 B2 * | 2/2018 | Fabrikant | ............... | H04W 4/029 |
| 9,996,668 B2 * | 6/2018 | Reihman | ................ | G16H 10/60 |
| 10,169,539 B2 * | 1/2019 | Reihman | ................ | G16H 15/00 |
| 10,483,000 B2 * | 11/2019 | Saint | ................ | G16H 20/17 |
| 10,592,914 B2 * | 3/2020 | Milton | ............... | G06Q 30/0205 |
| 10,713,672 B1 * | 7/2020 | Cranshaw | .......... | G06Q 30/0205 |
| D892,819 S * | 8/2020 | Mensinger | ................... | D14/485 |
| D893,020 S * | 8/2020 | Saint | ............................ | D24/113 |
| 10,754,927 B2 * | 8/2020 | Mensinger | ............. | G16H 10/60 |
| 10,864,327 B2 * | 12/2020 | Saint | .................... | A61M 5/3202 |
| D908,210 S * | 1/2021 | Saint | ............................ | D24/113 |
| 10,898,653 B2 * | 1/2021 | Saint | ................ | A61M 5/31568 |
| 11,093,561 B2 * | 8/2021 | Douze | .................... | G06Q 50/01 |
| 11,141,116 B2 * | 10/2021 | Cabrera, Jr. | ........... | G16H 15/00 |
| 11,369,743 B2 * | 6/2022 | Saint | ...................... | G08B 21/02 |
| 11,383,043 B2 * | 7/2022 | Sjolund | ................ | G16H 20/60 |
| D960,895 S * | 8/2022 | Mensinger | ................... | D14/485 |
| 11,464,459 B2 * | 10/2022 | Sjolund | ................ | G16H 40/67 |
| 11,484,657 B2 * | 11/2022 | Saint | ................ | A61M 5/31546 |
| 11,537,269 B2 * | 12/2022 | Wohlstadter | ......... | G06F 3/04886 |
| 11,547,805 B2 * | 1/2023 | Sjolund | ............... | A61M 5/3202 |
| 11,563,485 B2 * | 1/2023 | Saint | .................. | G16H 20/13 |
| 11,568,975 B2 * | 1/2023 | Saint | ................ | A61M 5/31565 |
| 11,587,663 B2 * | 2/2023 | Mensinger | ............. | G16H 40/63 |
| 11,628,255 B2 * | 4/2023 | Mensinger | ......... | A61M 5/31568 705/3 |
| 11,664,107 B2 * | 5/2023 | Saint | .................... | A61M 5/1723 726/4 |
| 11,709,999 B2 * | 7/2023 | Huang | .................... | G06F 16/29 707/732 |
| 11,771,835 B2 * | 10/2023 | Sjolund | ................ | A61B 5/4839 604/207 |
| 11,826,555 B2 * | 11/2023 | Saint | ...................... | G16H 50/20 |
| 11,844,923 B2 * | 12/2023 | Sjolund | .................. | A61B 5/746 |
| 11,878,151 B2 * | 1/2024 | Saint | ................ | A61M 5/31568 |
| 11,896,797 B2 * | 2/2024 | Sjolund | ................ | A61B 5/14532 |
| 11,904,145 B2 * | 2/2024 | Sjolund | ................ | A61B 5/4839 |
| 11,918,789 B2 * | 3/2024 | Sjolund | ............... | A61M 5/3202 |
| 11,931,188 B2 * | 3/2024 | Cabrera, Jr. | ........... | G16H 40/63 |
| 11,931,549 B2 * | 3/2024 | Sjolund | ............. | A61B 5/14532 |
| 11,944,465 B2 * | 4/2024 | Sjolund | ............. | A61B 5/14532 |
| 11,948,671 B2 * | 4/2024 | Pryor | ...................... | H04W 4/80 |
| 11,957,884 B2 * | 4/2024 | Sjolund | ................ | G16H 20/17 |
| 12,027,249 B2 * | 7/2024 | Saint | ................ | A61B 5/14532 |
| 2006/0204111 A1 * | 9/2006 | Koshi | ...................... | G06F 40/58 382/229 |
| 2010/0280782 A1 * | 11/2010 | Harper | ................. | A61B 5/1473 702/104 |
| 2013/0076531 A1 * | 3/2013 | San Vicente | .......... | H04W 76/25 340/870.02 |
| 2015/0359490 A1 * | 12/2015 | Massey | ................ | A61B 5/4839 600/300 |
| 2017/0116374 A1 * | 4/2017 | Wiedeback | ............ | G16H 10/60 |
| 2017/0124272 A1 * | 5/2017 | Reihman | ................ | G16H 40/67 |
| 2017/0124275 A1 * | 5/2017 | Reihman | ................ | G16H 15/00 |
| 2017/0124350 A1 * | 5/2017 | Reihman | ................ | A61B 5/746 |
| 2018/0042559 A1 * | 2/2018 | Cabrera, Jr. | ........... | G16H 50/30 |
| 2021/0200393 A1 * | 7/2021 | Wohlstadter | .......... | G06F 3/0485 |
| 2022/0150308 A1 * | 5/2022 | Hua | ........................ | H04W 4/38 |

* cited by examiner

EVALUATION SYSTEM BASED ON ANALYTE DATA

CROSS REFERENCE TO RELATED APPLICATIONS

This application is a continuation of, and claims priority to International Application No. PCT/CN2021/133303, filed on Nov. 25, 2021, which claims priority to Chinese Patent Application No. 202110998641.0, field on Aug. 27, 2021, the disclosure of which are incorporated by reference herein in their entireties.

FIELD OF THE DISCLOSURE

The disclosure relates generally to the field of medicine. More specifically, the disclosure relates to evaluation systems based on analyte data.

BACKGROUND

In some medical application scenarios, where monitoring analyte data is critical to health of users, a user's analyte data, such as glucose data, may be detected and/or monitored to determine if the user's analyte data is within a clinically safe range. For example, by monitoring glucose data, a diabetic patient may not only obtain glucose status in time, but may also determine from the glucose status whether and/or when it is necessary to reduce glucose concentration in the body or when additional glucose is needed to increase glucose concentration in the body.

Currently, in the clinic, multiple analyte indicators are often acquired from analyte data, and the condition of the user's analyte is evaluated based on multiple analyte indicators. However, these analyte indicators often require interpretation by professionals to be understood by users. Therefore, the readability of the analyte indicator needs to be improved.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, the disclosure provides an evaluation system based on analyte data, including a memory storing a program, a display, and a processor coupled with the memory and the display. The processor is configured to perform the following steps.

Receiving analyte data during a predetermined time period from an object to be tested. The analyte data includes a concentration of an analyte over time in the predetermined time period of the object to be tested and the predetermined time period includes a first time period and a second time period.

Acquiring a plurality of analyte indicators different from each other based on the analyte data.

Normalizing the plurality of analyte indicators to a predetermined range to acquire a plurality of normalized analyte indicators within the predetermined range;

Plotting a polygon pattern corresponding to the analyte data during the first time period as a target polygon pattern based on the plurality of normalized analyte indicators during the first time period.

Plotting a polygon pattern corresponding to the analyte data during the second time period as a reference polygon pattern based on the plurality of normalized analyte indicators during the second time period.

Taking a line segment between a vertex and a center point as an axis, the length of the axis reflecting each normalized analyte indicator and the center point of the target polygon pattern coinciding with the center point of the reference polygon pattern.

Displaying the target polygon pattern and the reference polygon pattern, by the display, to evaluate the target polygon pattern.

Optionally, in at least one of the target polygon pattern and the reference polygon pattern, angles formed between axes are adjacent to each other are substantially the same.

Optionally, for the same normalized analyte indicator, the axis of the target polygon pattern corresponding to the normalized analyte indicator is collinear with the axis of the reference polygon pattern corresponding to the normalized analyte indicator.

Optionally, the first time period is not less than 1 day, the second time period is not less than 1 day, and the length of the first time period is the same as the length of the second time period.

Optionally, the processor is further configured to plot a polygon pattern as a standard polygon pattern based on the predetermined range and the number of the plurality of analyte indicators. The length of each axis reflects the range value of the predetermined range. The center point of the standard polygon pattern coincides with the center point of the target polygon pattern. For the same normalized analyte indicator, the axis of the standard polygon pattern corresponding to the normalized analyte indicator is collinear with the axis of the target polygon pattern corresponding to the normalized analyte indicator.

Optionally, the processor is further configured to: take a point on an axis of the standard polygon pattern as a vertex and taking a center point of the standard polygon pattern as a center point; and plot a polygon pattern as an intermediate polygon pattern in a manner similar to the standard polygon pattern.

Optionally, the intermediate polygon pattern is lighter in color than the target polygon pattern.

Optionally, if the closer to the center point in the target polygon pattern represents the worse the analyte indicator is, the larger the area of the target polygon pattern represents the better the analyte is; and if the closer to the center point in the target polygon pattern represents the better the analyte indicator is, the smaller the area of the target polygon pattern represents the better the analyte is.

Optionally, in at least one of the target polygon pattern and the reference polygon pattern: scales are drawn for axes at different predetermined intervals and each predetermined interval increases or decreases from the center point to the vertex.

Optionally, each of the predetermined intervals increases proportionally or differentially along a direction in which better analyte indicators are indicated in at least one of the target polygon pattern and the reference polygon pattern.

Optionally, the analyte is glucose, the plurality of analyte indicators include a first indicator, a second indicator, and a third indicator, the first indicator reflects a risk of low glucose, the second indicator reflects a compliance rate of glucose during a corresponding time period, and the third indicator corresponding to average glucose.

Optionally, the plurality of analyte indicators further include a fourth indicator and a fifth indicator. The fourth indicator reflects overall level and fluctuations of glucose. The fifth indicator reflects the rate of change of average glucose.

Optionally, the plurality of analyte indicators further include a sixth indicator, a seventh indicator, and an eighth indicator. The sixth indicator reflects glucose fluctuations due to physiological factors. The seventh indicator reflects glucose fluctuations due to user behavior. The eighth indicator reflects a risk of high glucose.

Optionally, the processor is configured to perform a weighted average on the normalized first indicator, the second indicator, the third indicator, the fourth indicator, the fifth indicator, the sixth indicator, the seventh indicator, and the eighth indicator to acquire an average indicator value. The processor is configured to evaluate a situation of the analyte based on the average indicator value. Weights of the first indicator, the second indicator, the third indicator, the fourth indicator, the fifth indicator, the sixth indicator, the seventh indicator, and the eighth indicator decrease successively.

Optionally, in the target polygon pattern, a part between the boundary and the center point of the target polygon pattern is filled with a gradient color. In the reference polygon pattern, a part between the boundary and the center point of the reference polygon pattern is filled with a gradient color. A standard polygon pattern is lighter in color than the target polygon pattern.

Optionally, the predetermined range is 0 to 10.

Optionally, the processor is further configured to receive a plurality of analyte data during a predetermined time period from a plurality of objects to be tested to acquire a plurality of target polygon patterns and to rank the axis lengths corresponding to the same normalized analyte indicator in the target polygon patterns of the plurality of objects to be tested.

Optionally, the processor is further configured to create a reminder message based on the ranking and to output the reminder message to the plurality of objects to be tested.

Optionally, at least one of the target polygon pattern and the reference polygon pattern is a triangle, a quadrilateral, a pentagon, a hexagon, a heptagon, an octagon, or a nonagon In some embodiments, the present disclosure provides an evaluation system based on analyte data including a memory storing a program, a display, and a processor coupled with the memory and the display. The processor is configured to receive analyte data from an object to be tested during a predetermined time period when the program is run by the processor. The analyte data includes a time dependent analyte concentration of the object to be tested in the predetermined time period, the predetermined time period includes a first time period and a second time period; to acquire a plurality of analyte indicators based on the analyte data, each of which is different from the others; to normalize the plurality of analyte indicators to a predetermined range to acquire a plurality of normalized analyte indicators within the predetermined range; to plot a polygon pattern corresponding to the analyte data during the first time period as a target polygon pattern based on the plurality of normalized analyte indicators during the first time period, plot a polygon pattern corresponding to the analyte data during the second time period as a reference polygon pattern based on the plurality of normalized analyte indicators during the second time period, and in the polygon patterns, when a line segment between a vertex and a center point is taken as an axis, the length of each axis reflects each of the normalized analyte indicators, the center point of the target polygon pattern coincides with the center point of the reference polygon pattern, and the display displays the target polygon pattern and the reference polygon pattern so that the target polygon pattern is evaluated.

In the present disclosure, a plurality of analyte indicators are acquired based on analyte data of different time periods, the plurality of analyte indicators are normalized to acquire a plurality of normalized analyte indicators within a predetermined range, a plurality of polygon patterns for different time periods are acquired based on the corresponding normalized analyte indicators of different time periods, the polygon pattern of one of the time periods is evaluated using the polygon patterns of the different time periods, and the situation of the analyte may be obtained intuitively compared with the analyte indicators. Thus, the readability of the analyte indicators may be improved.

Further, in the evaluation system of the present disclosure, optionally, in the polygon pattern, angles formed between axes adjacent to each other are substantially the same. Thus, the polygon pattern may be more easily plotted and the individual analyte indicator may be compared more intuitively.

Optionally, in the evaluation system of the present disclosure, optionally, for the same normalized analyte indicator, the axis of the target polygon pattern corresponding to the normalized analyte indicator is collinear with the axis of the reference polygon pattern corresponding to the normalized analyte indicator. Thus, the difference between the target polygon pattern and the reference polygon pattern of each analyte indicator may be intuitively obtained.

Optionally, in the evaluation system of the present disclosure, optionally, the first time period is not less than 1 day, the second time period is not less than 1 day, and the length of the first time period is equal to the length of the second time period. Thereby, it is subsequently possible to better evaluate the target polygon pattern corresponding to the first time period based on the reference polygon pattern corresponding to the second time period.

Optionally, in the evaluation system of the present disclosure, optionally, plotting a polygon pattern as a standard polygon pattern is plotted based on the predetermined range and the number of the plurality of analyte indicators, the length of each axis reflects the range value of the predetermined range, the center point of the standard polygon pattern coincides with the center point of the target polygon pattern, and for the same normalized analyte indicator, the axis of the standard polygon pattern corresponding to the normalized analyte indicator is collinear with the axis of the target polygon pattern corresponding to the normalized analyte indicator. In this case, the difference between the target polygon pattern and the standard polygon pattern of each analyte indicator may be obtained, and the proximity of the target polygon pattern to the standard polygon pattern may be intuitively determined. Thereby, an improved space of the analyte with respect to the best or the worst value may be obtained.

Further, in the evaluation system according to the present disclosure, optionally, if it is set that the closer to the center point in the target polygon pattern, the worse the analyte indicator is, the larger area of the target polygon pattern indicates the better situation of the analyte; if it is set that the closer to the center point in the target polygon pattern, the better the analyte indicator is, the smaller area of the target polygon pattern indicates the better situation of the analyte. Thus, the situation of the analyte may be obtained intuitively.

Further, in the evaluation system according to the present disclosure, optionally, in the polygon pattern, scales are drawn for axes at different predetermined intervals, and each predetermined interval increases or decreases from the center point to the vertex. In this case, a relatively good range of the analyte indicator may be refined. Thus, the visual effect may be improved.

Further, in the evaluation system according to the present disclosure, optionally, each of the predetermined intervals increases proportionally or differentially along a direction that indicates better analyte indicators in the polygon pattern. In this case, a relatively good or good range of the analyte indicator may be refined, which may reflect the small change of the analyte indicator. Thus, the visual effect may be improved.

Further, in the evaluation system according to the present disclosure, optionally, a point on an axis of the standard polygon pattern is taken as a vertex, and the center point of the standard polygon pattern is taken as a center point, a polygon pattern is plotted as an intermediate polygon pattern in a manner similar to the standard polygon pattern. Thus, the target of periodical analyte improvement may be obtained based on the intermediate polygon pattern.

Further, in the evaluation system according to the present disclosure, optionally, the analyte is glucose, and the plurality of analyte indicators include a first indicator reflecting a risk of low glucose, a second indicator reflecting a compliance rate of glucose over a corresponding time period, and a third indicator corresponding to average glucose. Thus, a triangle may be obtained based on the plurality of analyte indicators.

Further, in the evaluation system according to the present disclosure, optionally, the plurality of analyte indicators also includes a fourth indicator reflecting the overall level and fluctuations of glucose and a fifth indicator reflecting the rate of change of average glucose. Thus, a pentagon may be obtained based on the plurality of analyte indicators.

Further, in the evaluation system according to the present disclosure, optionally, the plurality of analyte indicators also includes a sixth indicator reflecting glucose fluctuations due to physiological factors, a seventh indicator reflecting glucose fluctuations due to user behaviors, and an eighth indicator reflecting a risk of high glucose. Thus, an octagon may be obtained based on the plurality of analyte indicators.

Further, in the evaluation system according to the present disclosure, optionally, the processor is further configured to perform a weighted average on the plurality of normalized analyte indicators of the object to be tested to acquire an average indicator value, and to evaluate the situation of the analyte based on the average indicator value. Thus, the situation of the analyte may be evaluated based on the average indicator value.

Further, in the evaluation system according to the present disclosure, optionally, the processor is further configured to perform a weighted average on the first indicator, the second indicator, the third indicator, the fourth indicator, the fifth indicator, the sixth indicator, the seventh indicator and the eighth indicator which are normalized to acquire an average indicator value, and to evaluate the situation of the analyte based on the average indicator value. The weights of the first indicator, the second indicator, the third indicator, the fourth indicator, the fifth indicator, the sixth indicator, the seventh indicator and the eighth indicator decrease successively. In this case, when the average indicator value is calculated, the contribution of the more important indicator to the average indicator value may be increased and the influence of the relatively unimportant indicator on the average indicator value may be suppressed.

Further, in the evaluation system according to the present disclosure, optionally, in the target polygon pattern, the part from the boundary to the center point of the target polygon pattern is filled with a gradient color, and in the reference polygon pattern, the part from the boundary to the center point of the reference polygon pattern is filled with a gradient color. Thus, the visual effect may be improved.

Further, in the evaluation system according to the present disclosure, optionally, the standard polygon pattern is lighter in color than the target polygon pattern. Thus, the target polygon pattern may be highlighted.

Further, in the evaluation system according to the present disclosure, optionally, the predetermined range is 0 to 10.

Further, in the evaluation system according to the present disclosure, optionally, the processor is further configured to receive a plurality of analyte data from a plurality of objects to be tested during a predetermined time period to acquire a plurality of target polygon patterns, and to rank the axis lengths corresponding to the same normalized analyte indicator of the target polygon patterns of the plurality of objects to be tested. In this case, the ranking of each normalized analyte indicator may be used to increase the users' enthusiasm in improving the corresponding indicator.

In addition, in the evaluation system according to the present disclosure, optionally, a weighted average is performed on a plurality of normalized analyte indicators of each object to be tested to acquire an average indicator value, and the average indicator values of all objects to be tested are ranked. Thus, the users' enthusiasm for improving the situation of the analyte may be increased.

In addition, in the evaluation system according to the present disclosure, optionally, reminder messages based on the ranking are created and the reminder messages to the plurality of objects to be tested are output.

BRIEF DESCRIPTION OF THE DRAWINGS

Illustrative embodiments of the present disclosure are described in detail below with reference to the attached drawing figures.

DETAILED DESCRIPTION

Figure 1:
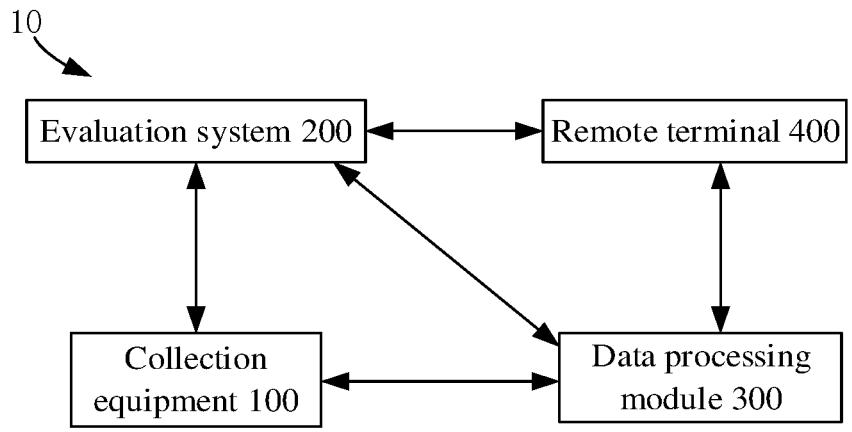
FIG. 1 is a schematic diagram illustrating a monitoring system based on analyte data according to an example of the present disclosure.

The following describes some non-limiting exemplary embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

The analyte collection equipment of the disclosed examples may be configured to collect analyte data. In some examples, the analyte collection equipment may be an in vivo analyte collection equipment. In some examples, the in vivo analyte collection equipment may be configured such that at least a portion is located in the body of the object to be tested. Thus, analyte data may be obtained. In some examples, an in vivo analyte collection equipment may include an in vivo analyte sensor and an electronic equipment disposed on a body, such as on a skin surface, and the in vivo analyte sensor may sense analyte data and transmit it to the electronic equipment on the body.

In some examples, the analyte collection equipment may be a continuous glucose monitoring system. In this case, the analyte collection equipment may periodically measure and record analyte data. For example, the analyte collection equipment may measure and record analyte data every 1, 2, 3, 5, 15, or 20 minutes.

However, the disclosed examples are not limited to these, and in other examples, the analyte collection equipment may be any device capable of obtaining analyte data. For example, the analyte collection equipment may be a device that detects an analyte separated from a human body. The analyte collection equipment may have a port for receiving an analyte. Specifically, the analyte may be placed on a support medium, such as a test strip, and the support medium may then be inserted into a port for detecting the analyte, thereby obtaining analyte data. In other examples, the analyte collection equipment may also be configured to acquire analyte data from other systems and/or via the user's own reporting.

In some examples, analyte data for a corresponding time period may be stored according to the hardware capabilities of the analyte collection equipment, such as the size of the memory.

In some examples, the analyte collection equipment may transmit collected analyte data to an evaluation system. In some examples, the analyte collection equipment may transmit the collected analyte data to a data processing module (described hereinafter) for processing and analysis by the data processing module prior to transmitting to an evaluation system.

The evaluation system to which the disclosed examples relate may have a memory, a display and a processor. The memory of the evaluation system may be configured to store programs (i.e. software algorithms). When a program is run by a processor, a corresponding control command may be generated. For example, an executing software algorithm may receive analyte data and process the analyte data. When executed by the processor, the program may also respond to a request from an input module on the evaluation system, such as a hardware button, a touch screen, or a sound device. For example, the sound device may include a microphone and a speaker. The display of the evaluation system, which may also be referred to as a display device, may be configured to deliver corresponding information, e. g. warning information, to a user, e. g. an object to be tested, in the form of visual feedback. In some examples, the display may be a touch screen. However, the disclosed examples are not limited to these, and in other examples, the evaluation system may deliver corresponding information in the form of tactile feedback. For example, the evaluation system may use the vibration output assembly to deliver corresponding information in the form of vibration.

In some examples, the evaluation system may include one or more wired or wireless communication ports that may be configured to establish communication between the evaluation system and other units, such as an analyte collection equipment, a data processing module, or a remote terminal (described hereinafter).

For ease of description, examples of the present disclosure are described below primarily with reference to the analyte being glucose, and such description is not intended to limit the scope of the present disclosure. The monitoring systems of the present disclosure may be configured to monitor various analytes simultaneously or at different times. The evaluation system may be configured to evaluate the various analytes simultaneously or at different times. For example, analytes may include, but are not limited to, glucose, growth hormone, cholesterol, glutamine, acetylcholine, amylase, bilirubin, cholesterol, fructosamine, and the like. FIG. 1 is a schematic diagram illustrating monitoring system based on analyte data 10 according to an example of the present disclosure.

As shown in FIG. 1, in some examples, monitoring system 10 may include collection equipment 100, evaluation system 200, data processing module 300, and remote terminal 400.

In some examples, collection equipment 100 may be configured to collect analyte data and transmit it to evaluation system 200 and/or data processing module 300.

In some examples, evaluation system 200 may be configured to receive analyte data of collection equipment 100 and/or target data obtained by analysis via data processing module 300 and process to deliver corresponding information. For example, in the case that the analyte is glucose, the corresponding information delivered may include glucose concentration (e. g. a numerical value of the concentration of glucose may be displayed), a curve of glucose concentration over time, a rate of change in glucose concentration or a trend in the rate of change in glucose concentration, and warning information, etc. In some examples, evaluation system 200 may be configured to obtain a plurality of analyte indicators based on the analyte data, and deliver corresponding information based on the plurality of analyte indicators.

In some examples, the processor of evaluation system 200 may be configured to execute programs stored in the memory to process the analyte data and/or the target data to deliver corresponding information. In some examples, the display of evaluation system 200 may be configured to display the corresponding information delivered. In some examples, the display of evaluation system 200 may also be configured to display date information, time information, power usage, and the like.

In some examples, data processing module 300 may be configured to receive analyte data collected by collection equipment 100 and analyze the analyte data to acquire target data. For example, the target data may include a plurality of analyte indicators. In some examples, data processing module 300 may be integrated into evaluation system 200. In some examples, data processing module 300 may be configured to analyze the analyte data to acquire target data based on a machine learning algorithm.

In some examples, remote terminal 400 may be configured to receive data delivered by evaluation system 200 and/or data processing module 300 to monitor the situation of the analyte. That is, evaluation system 200 and/or data processing module 300 may transmit corresponding data to remote terminal 400. In some examples, remote terminal 400 may also be configured to export or print an analyte report. In some examples, remote terminal 400 may include, but is not limited to, a personal computer, a server terminal, a portable computer (e. g. a notebook computer), or other data processing devices. In some examples, remote terminal 400 may include software that processes and analyzes data and communicates with assemblies in monitoring system 10. For example, remote terminal 400 may be connected to a computer network. The computer network may include a local area network, a wide area network, or other data network.

In some examples, remote terminal 400 may be located at a location other than the location of evaluation system 200. In some examples, remote terminal 400 may be a computer terminal used by a guardian of an object to be tested (e. g. a patient). In some examples, remote terminal 400 may be a computer terminal used by a healthcare provider (e. g. a doctor). In some examples, evaluation system 200, data processing module 300, and/or remote terminal 400 may all receive analyte data and process the analyte data.

Hereinafter, evaluation system 200 based on analyte data according to the present disclosure will be described in detail with reference to the accompanying drawings. An evaluation system based on analyte data may simply be referred to as an evaluation system, an evaluation device, an evaluation equipment, a visualization equipment, or a monitoring device, etc. As described above, evaluation system 200 may be configured to evaluate various analytes simultaneously or at different times. The case that the analyte is glucose is taken as an example in the description hereinafter. In some examples, a corresponding evaluation method may be implemented when a program stored in a memory of evaluation system 200 is run by a processor.

Figure 2:
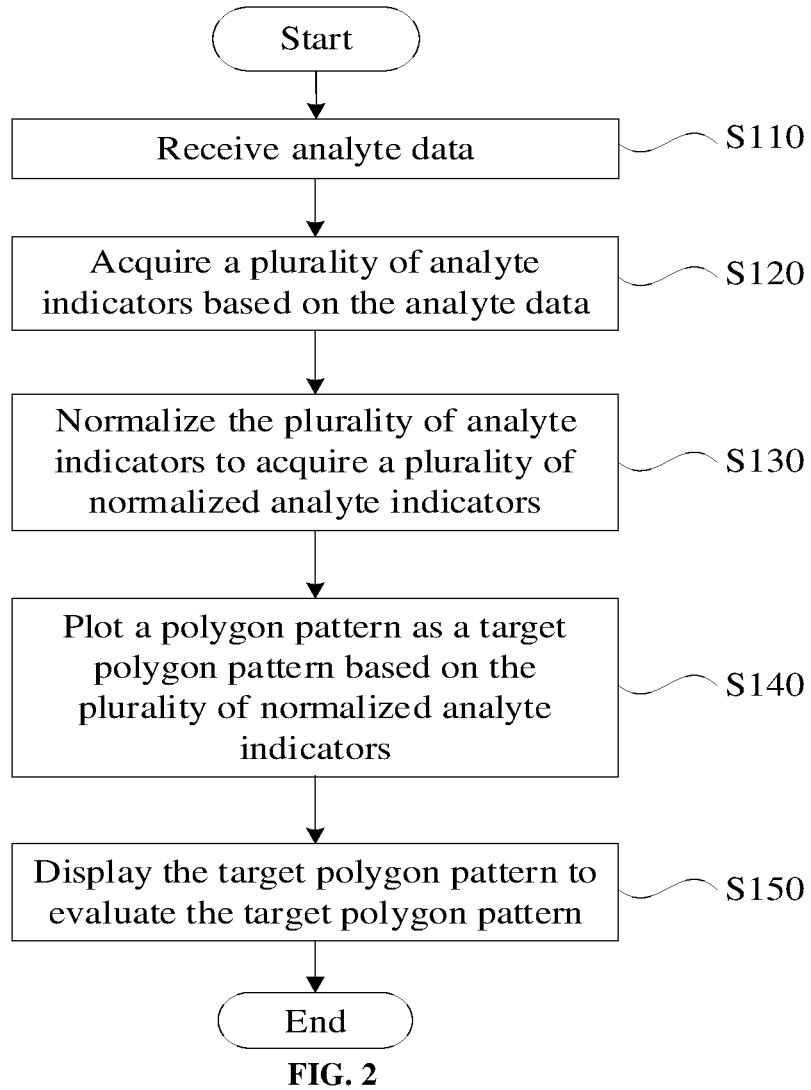
FIG. 2 is a flow chart illustrating an evaluation method based on analyte data according to an example of the present disclosure.

FIG. 2 is a flow chart illustrating an evaluation method based on analyte data according to an example of the present disclosure.

In some examples, as shown in FIG. 2, the evaluation method may include receiving analyte data (step S110). For example, the analyte data may be glucose data. In some examples, the analyte data may be from an object to be tested. However, the disclosed examples are not limited to these, the analyte data may come from any user capable of providing analyte data. In some examples, analyte data may be periodically measured and recorded by collection equipment 100 described above.

In some examples, analyte data during a predetermined time period may be received from an object to be tested. In some examples, the predetermined time period may include a first time period. In some examples, the first time period may be less than 1 hour, or may be greater than 1 hour. In some examples, the first time period may be no less than 1 day. For example, the first time period may be 1 day, 3 days, 5 days, 7 days, 10 days, 14 days, 3 weeks, or 1 month, etc.

In some examples, the analyte data may include an analyte concentration. For example, the analyte concentration may be a glucose concentration (which may also be referred to as a glucose level). In some examples, the analyte data may include the analyte concentrations of the object to be tested over time during a predetermined time period. In some examples, the analyte data may include the analyte concentrations of the object to be tested over time during a first period of the predetermined time periods. In some examples, the analyte data may include the analyte concentrations of the object to be tested over time during a second period (described hereinafter) of the predetermined time periods.

In some examples, the analyte data may include continuous analyte concentrations. For example, the analyte data may be continuous glucose concentrations.

In some examples, as shown in FIG. 1, the evaluation method may include acquiring a plurality of analyte indicators based on the analyte data (step S120). In some examples, the analyte indicators may differ from each other. That is, the analyte indicators may be obtained based on different analytical methods. In some examples, the analyte indicators may reflect the situation of the analyte from different dimensions.

In some examples, a plurality of analyte indicators for a first time period may be acquired based on the analyte data corresponding to a first time period of a predetermined time period. In some examples, the first time period may include a plurality of time scales. For example, the time scale may be in units of minutes, hours, days, or weeks, etc. For example, if the first time period is 14 days and 1 day is a time scale, there are 14 time scales within the first time period. In some examples, analyte concentrations at the same moment over multiple time scales may be analyzed to acquire analyte indicators. For example, if the time scale is one day, the analyte concentrations at the same moment of each day may be analyzed to acquire analyte indicators. In some examples, the interval of the adjacent same moments may correspond to moments at which analyte data is collected. In some examples, the interval of the adjacent same moments may also be a predetermined multiple of the period over which analyte data is collected. For example, if collection equipment 100 collects analyte data for a period of 5 minutes (i. e. collect an analyte concentration for 5 minutes), the interval between the adjacent same time points may be 5 minutes, 10 minutes, or 15 minutes, etc.

Figure 3:
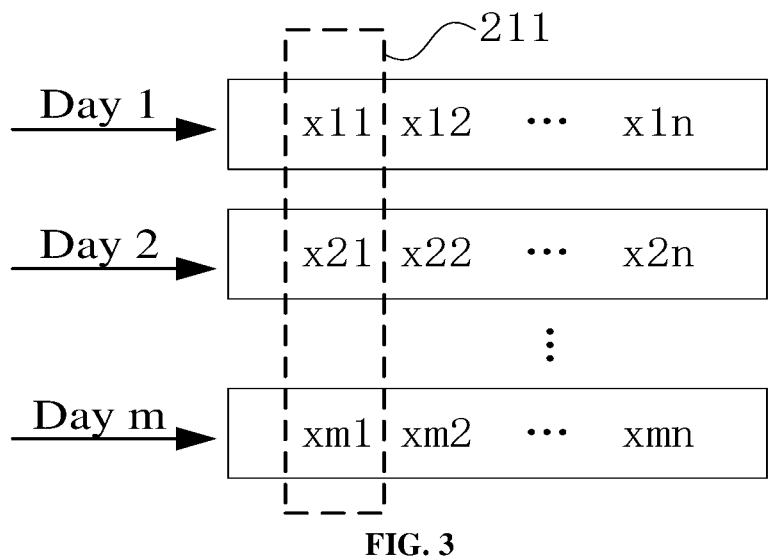
FIG. 3 is a schematic diagram illustrating analyte concentrations at the same moment according to an example of the present disclosure.

FIG. 3 is a schematic diagram illustrating analyte concentration at the same moment according to an example of the present disclosure.

As an illustration of the analyte concentration at the same moments, as shown in FIG. 3, assuming that the time scale is one day, the analyte data collected every day includes n analyte concentrations corresponding to n moments, the analyte concentrations at each moment on the first day are x11, x12, . . . , x1n respectively, the analyte concentrations at each moment on the second day are x21, x22, . . . , x2n respectively, and the analyte concentrations at each moment on the $m^{th}$ day are xm1, xm2, . . . , xmn respectively, the analyte concentrations at the first moments of all days are x11, x21, ..., xm1, that is, the analyte concentrations identified by block 211. It is similar to other analyte concentrations at other same moments.

In some examples, the number of analyte concentrations at the same moments during the first one of the predetermined time periods may be equal to the number of time scales during the first one of the predetermined time periods. For example, if the first time period is five days and one day is a time scale, there are five time scales within the first time period, and the number of analyte concentrations at the same moments may be five. That is, five analyte concentrations may be obtained at a moment to acquire analyte indicators.

As described above, in some examples, analyte concentrations at the same moment over multiple time scales may be analyzed to acquire an analyte indicator. However, the examples of the present disclosure are not limited to these, in some examples, an analyte indicator may be acquired based on all analyte concentrations in the analyte data (i. e. the analysis may not be performed according to time scales). In some examples, all analyte concentrations in the analyte data may be averaged to acquire an average analyte concentration. In some examples, an analyte compliance rate may be acquired based on the ratio of the time when the analyte concentration in the analyte data is within the target range to the time period corresponding to the analyte data (e. g. the first time period).

In some examples, the target range may be a safe range of analyte concentrations. That is, the analyte concentrations within the target range may be considered to be those of a normal user. In some examples, the target range may be from a lower limit of the target analyte to an upper limit of the target analyte. In some examples, the lower limit of the target analyte may be 3.9 mmol/L and the upper limit of the target analyte may be 10 mmol/L for glucose as the analyte. The lower limit of the target analyte and the upper limit of the target analyte may be adjusted based on units.

Figure 4:
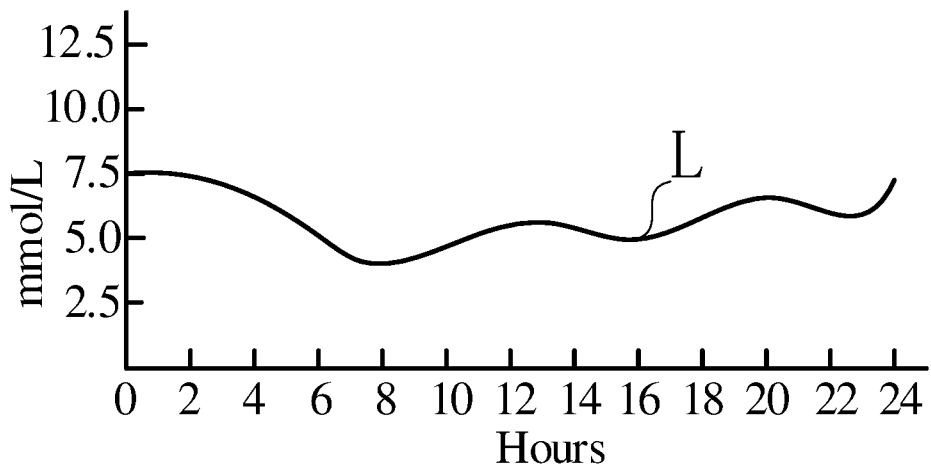
FIG. 4 is a schematic diagram illustrating the variation trend of moment analyte indicators over time according to an example of the present disclosure.

FIG. 4 is a schematic diagram illustrating the variation trend of the moment analyte indicators over time according to an example of the present disclosure.

As described above, in some examples, analyte concentrations at the same moment over multiple time scales may be analyzed to acquire an analyte indicator. In some examples, at least one moment analyte indicator for the same moment may be acquired based on the analyte concentrations at the same moment. In some examples, an analyte indicator may be acquired based on a plurality of analyte indicators at a same moment. In some examples, a plurality of moment analyte indicators may be averaged to acquire an analyte indicator. In some examples, the analyte indicators at a same moment may be fitted to acquire an analyte curve, and the analyte indicators may be acquired based on the analyte curve. The analyte curve may reflect the trend of the moment analyte indicator over time, and FIG. 4 shows an example of an analyte curve L.

In some examples, the analyte curve may be smoothed to acquire a smoothed analyte curve, and the analyte indicator may then be acquired based on the smoothed analyte curve. Thus, the corresponding analyte indicator may be more accurately calculated based on the smoothed analyte curve. It should be noted that, unless otherwise specified, subsequent acquisition of an analyte indicator based on an analyte curve is equally applicable to a smoothed analyte curve.

In some examples, an moment analyte indicator may include a median (also referred to as a median). In some examples, analyte concentrations at a same moment may be ranked to acquire an intermediate analyte concentration as a median. In some examples, if there are two values for the intermediate analyte concentration, the average of the two values may be taken as the median.

In some examples, a moment analyte indicator may include a quantile value. The quantile value may be the concentration of the analyte at a corresponding position in the concentration of the analyte at the same moment in order. In some examples, analyte concentrations at a same moment may be ranked to acquire ordered data, and a quantile value is acquired based on the ordered data.

In some examples, the quantile value may include at least one of quartiles, deciles, and each $20^{th}$ percentile. In some examples, when calculating the respective quantile value, the ordered data may be divided into fractions corresponding to the respective quantile value, two analyte concentrations of the first and last fractions closer to the middle are acquired, respectively, and the larger of the two analyte concentrations is taken as the upper quantile value and the other as the lower quantile value. For example, in calculating the quartiles, the ordered data may be divided into four quarters, the two analyte concentrations closer to the middle of the first and last portions are acquired, respectively, and the larger of the two analyte concentrations is taken as the upper quartile and the other as the lower quartile. The upper and lower deciles corresponding to the deciles and the upper and lower $20^{th}$ percentiles corresponding to the $20^{th}$ percentiles may be acquired based on the method consistent with the case of the quartiles.

In some examples, the mean value and standard deviation may be calculated based on the analyte concentration at the same moment, fitted using a normal distribution, and the larger one of the two values at the one-fourth and three-fourth positions in the list of values randomly generated by the normal distribution is taken as the upper quartile, and the other one is taken as the lower quartile. Similarly, the larger one of the two values at the tenth and ninth positions in the number list randomly generated by a normal distribution is taken as the upper decile, and the other value as the lower decile.

Figure 5:
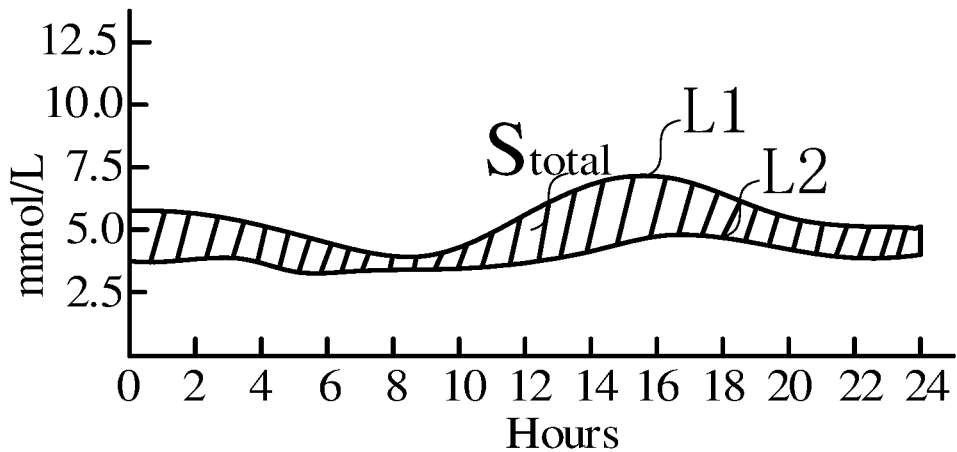
FIG. 5 is a schematic diagram illustrating the area enclosed by the analyte curve corresponding to the upper decile values and the analyte curve corresponding to the lower decile values according to an example of the present disclosure.

FIG. 5 is a schematic diagram illustrating the area $S_{total}$ enclosed by the analyte curve L1 corresponding to the upper decile and the analyte curve L2 corresponding to the lower decile according to an example of the present disclosure.

In some examples, if the analyte is glucose, the plurality of analyte indicators may include a first indicator, a second indicator, and a third indicator.

In some examples, the first indicator may reflect a risk of low glucose. As described above, in some examples, an analyte indicator may be acquired based on a plurality of moment analyte indicators at a same moment, which may include a quantile value which may include deciles, and the deciles may correspond to an upper decile and a lower decile. In some examples, the first indicator may be a ratio of an area under a straight line corresponding to a lower limit of the target analyte of the analyte curve corresponding to the lower decile to an area bounded by the analyte curve corresponding to the upper deciles and the analyte curve corresponding to the lower deciles.

In some examples, the first indicator may satisfy the following formula.

$$P_1 = \frac{1}{S_{total}} \times \sum_{i=1}^{K_1} |v_{lowi} - B_{low}| \times t$$

Here, $S_{total}$ represents the area enclosed by the analyte curve corresponding to the upper deciles and the analyte curve corresponding to the lower deciles, $K_1$ represents the number of the same moments when the lower deciles is smaller than the lower limit of the target analyte, i represents the index of the same moment when the lower deciles is smaller than the lower limit of the target analyte, $v_{lowi}$ represents the lower decile of the $i_{th}$ same moment, $B_{low}$ represents the lower limit of the target analyte, and t represents the interval between adjacent same moments. In some examples, t may be a predetermined multiple of the time scale of collecting analyte data described above.

Optionally, as an illustration of the area enclosed by the analyte curve corresponding to the upper deciles and the analyte curve corresponding to the lower deciles, as shown in FIG. 5, the analyte curve L1 corresponding to the upper deciles encloses the area $S_{total}$ with the analyte curve L2 corresponding to the lower deciles.

In some examples, the second indicator may reflect a compliance rate for glucose. In some examples, the second indicator may reflect a percentage of time when the target for glucose is reached within a corresponding time period (e. g. a time period corresponding to analyte data). In some examples, the second indicator may be the analyte compliance rate described above.

In some examples, the third indicator may correspond to average glucose. In some examples, the third indicator may be the average analyte concentration described above.

In some examples, if the analyte is glucose, the plurality of analyte indicators may further include a fourth indicator and a fifth indicator.

In some examples, the fourth indicator may reflect the overall level of glucose as well as glucose fluctuations. In some examples, the smaller the fourth indicator, the smaller the glucose fluctuation, the better the situation of the glucose may be indicated. In some examples, the fourth indicator may be the area under the analyte curve corresponding to the median value. In some examples, the fourth indicator may satisfy the following formula.

$$P_4 = \sum_{i=1}^{K_2} |V_{meani}| \times t$$

Here, $K_2$ represents the number of the same moments, i represents the index of the same moment, $v_{meani}$ represents the median of the $i_{th}$ same moment, and t represents the interval of adjacent same moments. In some examples, t may be a predetermined multiple of the time scale of collecting analyte data described above.

In some examples, the fourth indicator may be converted according to units. For example, if the unit of the fourth indicator is mg/dL/h, the fourth indicator $P_4$ may be divided by a number of hours, e. g. 24 hours, corresponding to one time scale, and the unit is not particularly limited by the present disclosure.

In some examples, the fifth indicator may reflect an average rate of change of glucose. In some examples, the fifth indicator may reflect a change in the analyte curve corresponding to the median value. In some examples, the fifth indicator may satisfy the following formula.

$$P_5 = \frac{1}{(K_3 - 1) \times t} \times \sum_{i=1}^{K_3-1} |v_{meani+1} - v_{meani}|$$

Here, $K_3$ represents the number of the same moments, t represents the interval of adjacent same moments, i represents the index of the same moment, $v_{meani+1}$ represents the median of the $i+1_{th}$ same moment, and $v_{meani}$ represents the median of the $i_{th}$ same moment. In some examples, t may be a predetermined multiple of the time scale of collecting analyte data described above.

In some examples, if the analyte is glucose, the plurality of analyte indicators may further include a sixth indicator, a seventh indicator, and an eighth indicator.

In some examples, the sixth indicator may reflect glucose fluctuations caused by physiological factors. For example, physiological factors may include islet function. In some examples, the sixth indicator may be an average of differences between the upper and lower quartile values corresponding to a plurality of quartile values at the same moment as described above.

In some examples, the seventh indicator may reflect glucose fluctuations caused by behavior of a user, e. g. an object to be tested. For example, user behavior may include diet, exercise, stress, etc. In some examples, the seventh indicator may be an average of the differences between the upper and lower deciles corresponding to the plurality of deciles at the same moment.

In some examples, the eighth indicator may reflect a risk of high glucose. In some examples, the eighth indicator may be a ratio of an area of the analyte curve corresponding to the upper deciles on a straight line corresponding to the upper limit of the target analyte to an area bounded by the analyte curve corresponding to the upper deciles and the analyte curve corresponding to the lower deciles.

In some examples, the eighth indicator may satisfy the following formula.

$$P_8 = \frac{1}{S_{total}} \times \sum_{i=1}^{K_4} |v_{highi-B_{high}}| \times t$$

Here, $S_{total}$ represents the area enclosed by the analyte curve corresponding to the upper deciles and the analyte curve corresponding to the lower deciles, $K_4$ represents the number of the same moments when the upper deciles is greater than the upper limit of the target analyte, i represents the index of the same moment when the upper decile is greater than the upper limit of the target analyte, $v_{highi}$ represents the upper decile of the $i_{th}$ same moment, $B_{high}$ represents the upper limit of the target analyte, and t represents the interval between adjacent same moments. In some examples, t may be a predetermined multiple of the time scale of collecting analyte data described above.

As described above, one or more of the first indicator, the second indicator, the third indicator, the fourth indicator, the fifth indicator, the sixth indicator, the seventh indicator, and the eighth indicator may be acquired based on the analyte data. In some examples, each analyte indicator may have a respective boundary value, and the boundary value may include a first extreme value representing the best analyte indicator and a second extreme value representing the worst analyte indicator. Boundary values may be obtained based on existing studies and clinical data. For example, the first indicator may have a first boundary value, the second indicator may have a second boundary value, the third indicator may have a third boundary value, the fourth indicator may have a fourth boundary value, the fifth indicator may have a fifth boundary value, the sixth indicator may have a sixth boundary value, the seventh indicator may have a seventh boundary value and the eighth indicator may have an eighth boundary value. For example, for an analyte that is glucose, for example, the first extreme value of the first boundary value may be 0 and the second extreme value of the first boundary value may be 30%.

In some examples, as shown in FIG. 2, the evaluation method may include normalizing a plurality of analyte indicators to acquire a plurality of normalized analyte indicators (step S130).

In some examples, in step S130, a plurality of analyte indicators may be normalized into a predetermined range to acquire a plurality of normalized analyte indicators within the predetermined range. As described above, in some examples, a plurality of analyte indicators for a first time period may be acquired based on analyte data corresponding to a first time period of a predetermined time period. In some examples, the plurality of analyte indicators during the first time period may be normalized to a predetermined range to acquire a plurality of normalized analyte indicators during the first time period within the predetermined range.

In some examples, the predetermined range may include both a initial value and an stop value. For example, the predetermined range may be 0 to 10. As another example, the predetermined range may be 0 to 100. In some examples, a initial value may be used to indicate that the analyte indicator is the worst and an stop value may be used to indicate that the analyte indicator is the best. That is, from the initial value to the stop value, the analyte indicator becomes better and better.

In some examples, when normalizing the analyte indicators, a corresponding section of the first extreme value and the second extreme value among the boundary values of the respective analyte indicators may be mapped to a corresponding section of the predetermined range to acquire a plurality of normalized analyte indicators within the predetermined range. For example, a first extreme value of the boundary values for each analyte indicator may correspond to one end value of the predetermined range, e. g. the stop value, and a second extreme value of the boundary values may correspond to another end value of the predetermined range, e. g. the initial value, and the analyte indicator may correspond to a corresponding value within the predetermined range.

In some examples, if the initial value of the predetermined range represents that the analyte indicator is the worst and the stop value of the predetermined range represents that the analyte indicator is the best, each normalized analyte indicator may satisfy the following formula:

$$C_{normalized} = \begin{cases} C_{end} & \text{If } P_{good} - P_{bad} > 0 \text{ and } P \geq P_{good} \\ C_{end} & \text{If } P_{good} - P_{bad} < 0 \text{ and } P \leq P_{good} \\ C_{begin} & \text{If } P_{good} - P_{bad} > 0 \text{ and } P \leq P_{bad} \\ C_{begin} & \text{If } P_{good} - P_{bad} < 0 \text{ and } P \geq P_{bad} \\ \frac{C_{end} - C_{begin}}{P_{good} - P_{bad}} \times (P - P_{bad}) + C_{begin} & \text{else} \end{cases}$$

Here, $C_{normalized}$ represents the normalized analyte indicator, P represents the analyte indicator may be represented, $P_{good}$ represents the first extreme value, $P_{bad}$ represents the second extreme value, $C_{begin}$ represents the initial value of the predetermined range, and $C_{end}$ represents the stop value of the predetermined range. It should be noted that the above formula does not limit the present disclosure in any way.

While the examples of the present disclosure are not limited to these, in other examples, a initial value may be used to indicate that the analyte indicator is the best and an stop value may be used to indicate that the analyte indicator is the worst. That is, from the initial value to the stop value, the analyte indicator becomes increasingly worse. In this case, each normalized analyte indicator may satisfy the following formula.

$$C_{normalized} = \begin{cases} C_{begin} & \text{If } P_{good} - P_{bad} > 0 \text{ and } P \geq P_{good} \\ C_{begin} & \text{If } P_{good} - P_{bad} < 0 \text{ and } P \leq P_{good} \\ C_{end} & \text{If } P_{good} - P_{bad} > 0 \text{ and } P \leq P_{bad} \\ C_{end} & \text{If } P_{good} - P_{bad} < 0 \text{ and } P \geq P_{bad} \\ \frac{C_{begin} - C_{end}}{P_{good} - P_{bad}} \times (P - P_{bad}) + C_{end} & \text{else} \end{cases}$$

Here, $C_{normalized}$ represents the normalized analyte indicator, P represents the analyte indicator may be represented, $P_{good}$ represents the first extreme value, $P_{bad}$ represents the second extreme value, $C_{begin}$ represents the initial value of the predetermined range, and $C_{end}$ represents the stop value of the predetermined range. It should be noted that the above formula does not limit the present disclosure in any way.

In some examples, as shown in FIG. 2, the evaluation method may include plotting a polygon pattern as a target polygon pattern based on a plurality of normalized analyte indicators (step S140).

As described above, in some examples, the plurality of analyte indicators during the first time period may be normalized into a predetermined range to acquire a plurality of normalized analyte indicators during the first time period within the predetermined range. In some examples, a polygon pattern corresponding to analyte data for a first time period may be plotted as a target polygon pattern based on a plurality of normalized analyte indicators during the first time period.

In some examples, in a polygon pattern, the line segment between the vertex and the center point may be an axis. In some examples, the length of each axis may reflect each normalized analyte indicator. In some examples, the center point of the polygon pattern may be predetermined, the distance of the vertex from the center point (i. e. the length of each axis) may then be determined based on each normalized analyte indicator, the location of each vertex may then be determined, and the edges of the polygon pattern may be determined based on the location of each vertex. Thus, a polygon pattern may be obtained. In some examples, the length of each axis may correspond to each normalized analyte indicator.

In some examples, in the target polygon pattern, the boundary to the center point of the target polygon pattern may be filled with a gradient color. Thus, the visual effect may be improved.

In some examples, the angles formed between axes adjacent to each other may be substantially the same in a polygon pattern. That is, the axes may be uniformly distributed in the polygon pattern. Thus, the polygon pattern may be more easily plotted and the individual analyte indicator may be compared more intuitively.

In some examples, the center point of the polygon pattern may represent a first extreme value or a second extreme value. That is, the center point of the polygon pattern may indicate that the analyte indicator is the best or may indicate that the analyte indicator is the worst. In other words, closer to a center point in a polygon pattern, such as a target polygon pattern, may indicate a better analyte indicator or closer to the center point may indicate a worse analyte indicator.

In some examples, in a polygon pattern, a scale may be drawn at different predetermined intervals for an axis, and each predetermined interval may increase or decrease from a center point to a vertex. In this case, a relatively good range of the analyte indicator may be refined. Thus, the visual effect may be improved. In some examples, a scale may be drawn on at least one axis in a polygon pattern. In some examples, a scale may be drawn on at least one axis in a standard polygon pattern (described hereinafter). In some examples, the scale value of the scale may increase or decrease by a predetermined step size.

Figure 6:
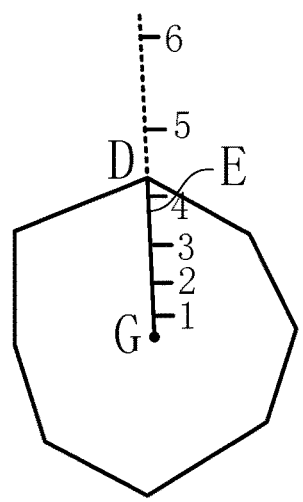
FIG. 6 is a schematic diagram illustrating various predetermined intervals increasing from a center point to a vertex according to an example of the present disclosure.

FIG. 6 is a schematic diagram illustrating various predetermined intervals increasing from a center point to a vertex according to an example of the present disclosure.

In some examples, each of the predetermined intervals may be decremented from the center point to the vertex if closer to the center point in the polygon pattern indicates better analyte indicators. In some examples, each of the predetermined intervals may increase from the center point to the vertex if closer to the center point in the polygon pattern indicates that the analyte indicator is worse. In general, analyte indicators are relatively good or more people are good. In this case, the relatively good or good range of the analyte indicator may be refined (i. e. the relatively good or good range of the analyte indicator may be distinguished), and minute changes in the analyte indicator may be reflected. Thus, the visual effect may be improved. As an example, as shown in FIG. 6, in the polygon pattern, the center point G may indicate that the analyte indicator is the worst, and the intervals of the scales 1, 2, 3, and 4 on the axis E are gradually increased from the center point G to the vertex D. In some examples, the plotting of the scale may continue on an extension of axis E, as shown in FIG. 6, the plotting of scale 5, scale 6, etc. In some examples, the polygon pattern may not show an axis.

In some examples, each of the predetermined intervals may increment proportionally or differentially along a direction in which better analyte indicators are indicated in a polygon pattern, such as a standard polygon pattern. Thus, different predetermined intervals may be conveniently provided.

Optionally, based on the equal-ratio increment, the predetermined interval may satisfy the following formula.

$$v_j + 1 = \frac{v_j}{V}$$

Here, V represents the coefficient representing an equal ratio increment, V may be a decimal number less than 1, j represents an index of a predetermined interval, $v_{j+1}$ represents the $j+1_{th}$ predetermined interval, and $v_j$ represents the $j_{th}$ predetermined interval. In some examples, the initial predetermined interval in the proportional increment (i. e. the first predetermined interval) may be a fixed value.

Optionally, based on the arithmetic increment, the predetermined interval may satisfy the following formula.

$$v_{j+1} = v_j + W$$

Here, W represents the step size representing an arithmetic increment, j represents an index of a predetermined interval, $v_{j+1}$ represents the $j+1_{th}$ predetermined interval, and $v_j$ represents the $j_{th}$ predetermined interval. In some examples, the initial predetermined interval in the equal-difference increment (i. e. the first predetermined interval) may be a fixed value.

In some examples, the polygon pattern may be a triangle (which may also be referred to as a three-dimensional graph), a quadrilateral (which may also be referred to as a four-dimensional graph), a pentagon (which may also be referred to as a five-dimensional graph), a hexagon (which may also be referred to as a six-dimensional graph), a heptagon (which may also be referred to as a seven-dimensional graph), an octagon (which may also be referred to as an eight-dimensional graph), or a nonagon (which may also be referred to as a nine-dimensional graph), etc.

In some examples, the number of sides of the polygon pattern may correspond to the number of multiple analyte indicators. Specifically, if the number of the plurality of analyte indicators is three, for example, the three analyte indicators may include a first indicator, a second indicator, and a third indicator, the polygon pattern may be a triangle. If the number of the plurality of analyte indicators is five, for example, the five analyte indicators may include a first indicator, a second indicator, a third indicator, a fourth indicator, and a fifth indicator, the polygon pattern may be a pentagon. If the number of the plurality of analyte indicators is eight, for example, the eight analyte indicators may include a first indicator, a second indicator, a third indicator, a fourth indicator, a fifth indicator, a sixth indicator, a seventh indicator, and an eighth indicator, the polygon pattern may be an octagon.

Figure 7A:
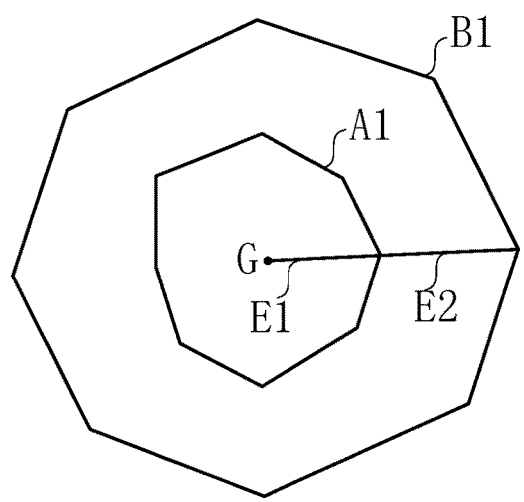
FIG. 7A is a schematic diagram illustrating a standard polygon pattern according to an example of the present disclosure.
Figure 7B:
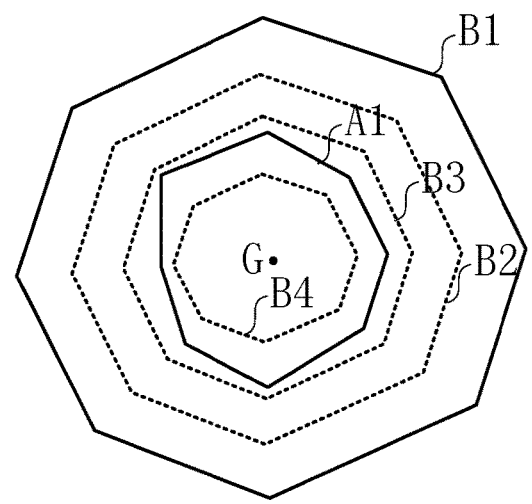
FIG. 7B is a schematic diagram showing an intermediate polygon pattern according to an example of the present disclosure.

FIG. 7A is a schematic diagram illustrating a standard polygon pattern according to an example of the present disclosure. FIG. 7B is a schematic diagram showing an intermediate polygon pattern according to an example of the present disclosure.

In some examples, a polygon pattern may be drawn as a standard polygon pattern based on a predetermined range and the number of the plurality of analyte indicators. In some examples, the length of each axis of a standard polygon pattern may reflect a range value of a predetermined range. In some examples, the length of each axis of the standard polygon pattern may correspond to a range value of a predetermined range. In some examples, the number of vertices of the standard polygon pattern may correspond to the number of multiple analyte indicators.

In some examples, the center point of the standard polygon pattern may coincide with the center point of the target polygon pattern. In some examples, a center point of the standard polygon pattern may coincide with a center point of the target polygon pattern, and an axis in the standard polygon pattern corresponding to the normalized analyte indicator and an axis in the target polygon pattern corresponding to the normalized analyte indicator may be collinear for the same normalized analyte indicator. In this case, the difference between the target polygon pattern and the standard polygon pattern of each analyte indicator may be obtained, and the proximity of the target polygon pattern to the standard polygon pattern may be intuitively determined. Thereby, an improved space with respect to the best or the worst analyte may be obtained. As an example, as shown in FIG. 7A, the center points of the target polygon pattern A1 and the standard polygon pattern B1 may both be center points G, and the axis E2 corresponding to the normalized analyte indicator in the standard polygon pattern B1 is collinear with the axis E1 corresponding to the normalized analyte indicator in the target polygon pattern A1.

In some examples, the names and units of corresponding analyte indicators may be drawn near the vertices of a standard polygon pattern. In some examples, the standard polygon pattern may be lighter in color than the target polygon pattern. Thus, the target polygon pattern may be highlighted.

In some examples, a polygon pattern may be drawn as an intermediate polygon pattern by taking a point on an axis as a vertex and taking a center point of the standard polygon pattern as a center point in a manner similar to the standard polygon pattern. That is, the intermediate polygon pattern may be a polygon pattern that conforms to the shape of the standard polygon pattern, but has an axis length smaller than the axis length of the standard polygon pattern. Thus, a target of periodical analyte improvement may be obtained based on the intermediate polygon pattern. In some examples, there may be multiple intermediate polygon patterns. As an example, as shown in FIG. 7B, for example, there are three intermediate polygon patterns within the standard polygon pattern B1, and the three intermediate polygon patterns may include an intermediate polygon pattern B2, an intermediate polygon pattern B3, and an intermediate polygon pattern B4. Here, in FIG. 7B, the intermediate polygon pattern is illustrated by a dotted line in order to better distinguish the intermediate polygon pattern from the standard polygon pattern B1 and the target polygon pattern A1, and does not represent a limitation to the present disclosure.

In some examples, the intermediate polygon pattern may be lighter in color than the target polygon pattern. Thus, the target polygon pattern may be highlighted.

In some examples, as shown in FIG. 2, the evaluation method may include displaying a target polygon pattern to evaluate the target polygon pattern (step S150). That is, the target polygon pattern may be visually evaluated. In some examples, the standard polygon pattern and/or the intermediate polygon pattern may be displayed simultaneously when the target polygon pattern is displayed. Thus, the target polygon pattern may be evaluated using more polygon patterns. In some examples, the display of evaluation system 200 may be configured to display the target polygon pattern. In some examples, the display of evaluation system 200 may be configured to simultaneously display the standard polygon pattern and/or the intermediate polygon pattern while displaying the target polygon pattern.

Figure 8A:
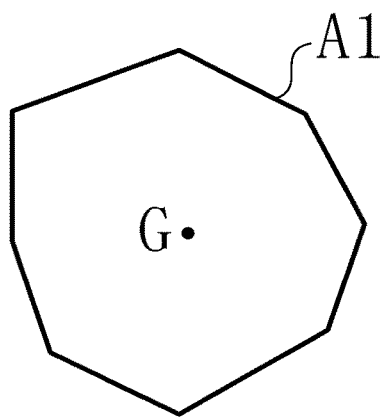
FIG. 8A is a schematic diagram illustrating a target polygon pattern according to an example of the present disclosure.
Figure 8B:
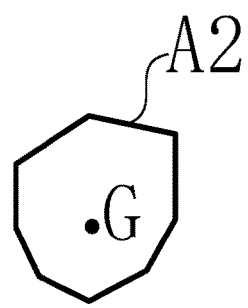
FIG. 8B is a schematic diagram illustrating another target polygon pattern according to an example of the present disclosure.

FIG. 8A is a schematic diagram illustrating a target polygon pattern according to an example of the present disclosure. FIG. 8B is a schematic diagram illustrating another target polygon pattern according to an example of the present disclosure.

In some examples, when the target polygon pattern is evaluated, the closer to the center point in the target polygon pattern, the worse the analyte indicator is represented, the better the area of the target polygon pattern represents the analyte. In some examples, the target polygon pattern may be evaluated such that the closer to a center point in the target polygon pattern, the better the analyte indicator is represented, and the smaller the area of the target polygon pattern, the better the analyte is represented. Thus, the situation of the analyte may be obtained intuitively. For example, as shown in FIGS. 8A and 8B, the target polygon pattern A2 is better than the analyte represented by the target polygon pattern A1 as the center point G is closer to represent the analyte indicator.

In some examples, the evaluation method may further include performing a weighted average of the plurality of normalized analyte indicators to acquire an average indicator value. The plurality of normalized analyte indicators may be derived from the object to be tested. That is, the processor of evaluation system 200 may also be configured to perform a weighted average on the plurality of normalized analyte indicators of the object to be tested to acquire an average indicator value. In some examples, the situation of the analyte may be evaluated based on an average indicator value. For example, where the analyte is glucose, it may be assessed whether there is an improvement in the condition of the glucose based on the magnitude of the mean indicator value. Thus, the situation of the analyte may be evaluated based on the average indicator value.

As described above, one or more of the first indicator, the second indicator, the third indicator, the fourth indicator, the fifth indicator, the sixth indicator, the seventh indicator, and the eighth indicator may be acquired based on the analyte data. The plurality of normalized analytes may be one or more of the normalized first, second, third, fourth, fifth, sixth, seventh, and eighth indicators. In some examples, the weights of the first indicator, the second indicator, the third indicator, the fourth indicator, the fifth indicator, the sixth indicator, the seventh indicator, and the eighth indicator may be sequentially decreased. In this case, when the average indicator value is obtained, the contribution of the more important indicator to the average indicator value may be increased and the influence of the relatively unimportant indicator on the average indicator value may be suppressed.

In some examples, the weights of the first indicator, the second indicator, the third indicator, the fourth indicator, the fifth indicator, the sixth indicator, the seventh indicator, and the eighth indicator may be sequentially reduced by equal ratios or by equal differences. In some examples, in the isopycnic reduction, the latter indicator may be a predetermined multiple of the former indicator, which may be less than 1. In some examples, in the equal difference reduction, the latter indicator may be smaller than the former indicator by a predetermined value, which may be greater than or equal to 1.

Figure 9:
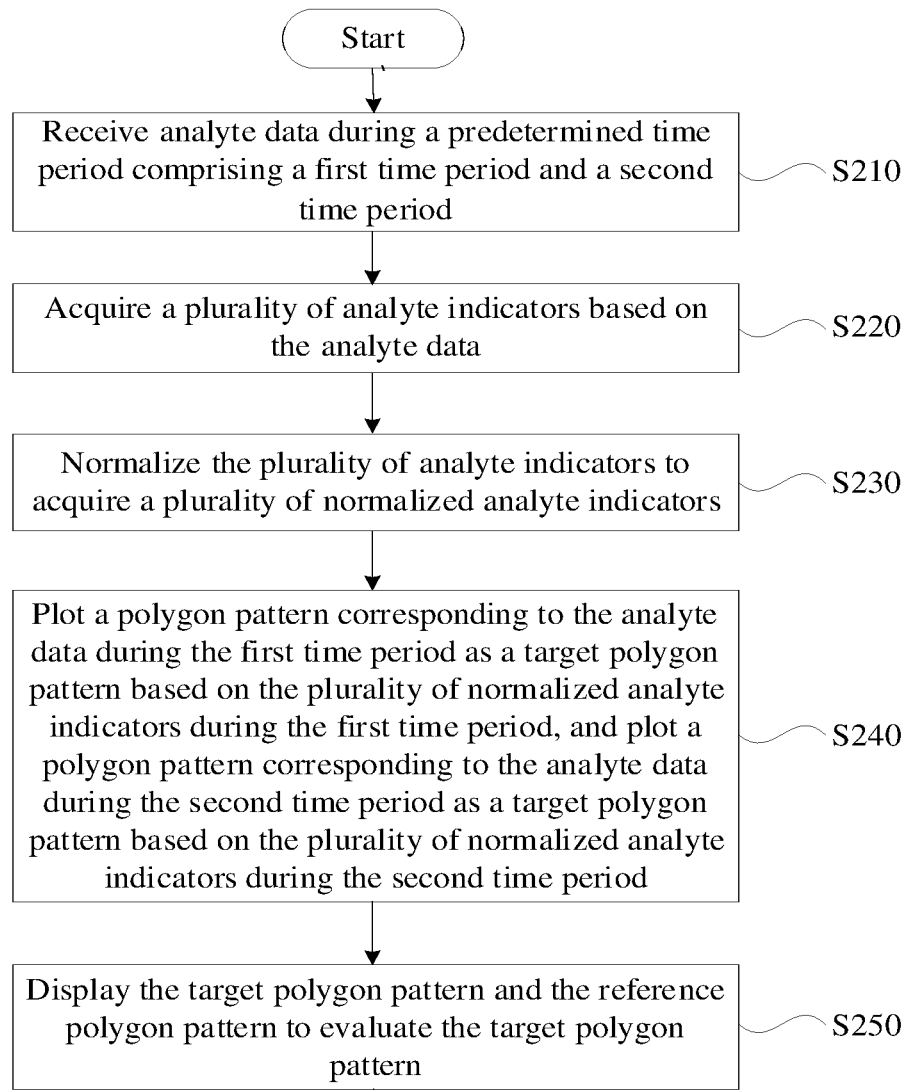
FIG. 9 is another flow chart illustrating an evaluation method based on analyte data according to an example of the present disclosure.

As described above, in some examples, the predetermined time period may include a first time period. In some examples, the predetermined time period may also include a second time period. That is, the predetermined time period may include a first time period and a second time period. The evaluation method for the first time period and the second time period is described below with reference to FIG. 9. It should be noted that the above description of the first time period in the evaluation method is also applicable to the second time period and will not be repeated here, unless otherwise specified. FIG. 9 is another flow chart illustrating an evaluation method based on analyte data according to an example of the present disclosure.

In some examples, the evaluation method may include receiving analyte data from the object to be tested during a predetermined time period. The predetermined time period includes a first time period and a second time period (step S210). In some examples, the analyte data may include the analyte concentration of the object to be tested over time during a predetermined time period. In some examples, the length of the first time period may be the same as the length of the second time period. Thereby, it is subsequently possible to better evaluate the target polygon pattern corresponding to the first time period based on the reference polygon pattern corresponding to the second time period. In some examples, the second time period may be no less than 1 day. In some examples, the second time period may be earlier in time than the first time period. However, the examples of the present disclosure are not limited thereto, and in other examples, the predetermined time period may further include a third time period, a fourth time period, a fifth time period, etc. See the relevant description in step S110 for details.

In some examples, the evaluation method may include acquiring a plurality of analyte indicators based on the analyte data (step S220). In some examples, in step S220, a plurality of analyte indicators for a first time period may be acquired based on analyte data corresponding to a first time period of the predetermined time period, and a plurality of analyte indicators for a second time period may be acquired based on analyte data corresponding to a second time period of the predetermined time period. The specific contents of acquiring a plurality of analyte indicators based on the analyte data are described in step S120.

In some examples, the evaluation method may include normalizing the plurality of analyte indicators to acquire a plurality of normalized analyte indicators (step S230). In some examples, the plurality of analyte indicators during the first time period may be normalized to a predetermined range to acquire a plurality of normalized analyte indicators during the first time period within the predetermined range, and the plurality of analyte indicators during the second time period may be normalized to the predetermined range to acquire a plurality of normalized analyte indicators during the second time period within the predetermined range. See the relevant description in step S130 for the specific content of normalization.

In some examples, the evaluation method may include plotting a polygon pattern corresponding to the analyte data during the first time period as a target polygon pattern based on the plurality of normalized analyte indicators during the first time period and plotting a polygon pattern corresponding to the analyte data during the second time period as a reference polygon pattern based on the plurality of normalized analyte indicators during the second time period (step S240). The specific content of plotting the polygon pattern based on the plurality of normalized analyte indicators is described in step S140.

In some examples, in step S240, in the reference polygon pattern, the part from the boundary to the center point of the reference polygon pattern may be filled with a gradient color. Thus, the visual effect may be improved. In some examples, the gradient color of the target polygon pattern and the reference polygon pattern may be the same. In some examples, the gradient color of the target polygon pattern and the reference polygon pattern may be different. Thus, it is possible to easily distinguish the target polygon pattern from the reference polygon pattern.

Figure 10:
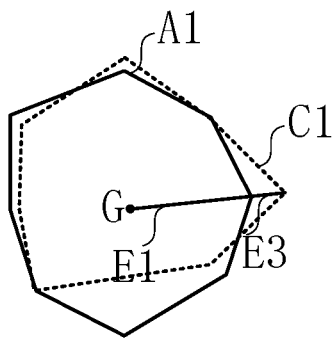
FIG. 10 is a schematic diagram illustrating a reference polygon pattern according to an example of the present disclosure.

FIG. 10 is a schematic diagram illustrating a reference polygon pattern according to an example of the present disclosure.

In some examples, the center point of the target polygon pattern may coincide with the center point of the reference polygon pattern. In this case, the difference between the target polygon pattern and the reference polygon pattern may be obtained intuitively. Thus, an improvement in the situation of the analyte during the first time period over the second time period may be obtained.

In some examples, the axis in the target polygon pattern corresponding to the normalized analyte indicator and the axis in the reference polygon pattern corresponding to the normalized analyte indicator may be collinear for the same normalized analyte indicator. Thus, the difference between the target polygon pattern and the reference polygon pattern of each analyte indicator may be intuitively obtained. As an example, as shown in FIG. 10, the center points of the target polygon pattern A1 and the reference polygon pattern C1 coincide in the center point G, and the axis E3 corresponding to the normalized analyte indicator in the reference polygon pattern C1 is collinear with the axis E1 corresponding to the normalized analyte indicator in the target polygon pattern A1. It should be noted that the dotted line is for better distinguishing the target polygon pattern A1 and the reference polygon pattern C1 and does not represent a limitation to the present disclosure.

In some examples, the evaluation method may include displaying the target polygon pattern and the reference polygon pattern to evaluate the target polygon pattern (step S250). In some examples, the standard polygon pattern and/or the intermediate polygon pattern may be displayed simultaneously when the target polygon pattern and the reference polygon pattern are displayed. Thus, the target polygon pattern may be evaluated using more polygon patterns. In some examples, the display of evaluation system 200 may be configured to display the target polygon pattern and the reference polygon pattern. In some examples, the display of evaluation system 200 may be configured to simultaneously display the standard polygon pattern and/or the intermediate polygon pattern while displaying the target polygon pattern and the reference polygon pattern. Thus, the target polygon pattern may be evaluated using more polygon patterns.

In some examples, it may be determined whether the situation of the analyte corresponding to the target polygon pattern is improved relative to the situation of the analyte corresponding to the reference polygon pattern by the reference polygon pattern.

In some examples, when the target polygon pattern is evaluated, the closer to the center point in the target polygon pattern indicates that the analyte indicator is worse, and if the area of the target polygon pattern is larger than the area of the reference polygon pattern, it may indicate that the situation of the analyte of the first time period is improved relative to the second time period. In some examples, when the target polygon pattern is evaluated, the closer to the center point in the target polygon pattern, the better the analyte indicator is represented, and if the area of the target polygon pattern is smaller than the area of the reference polygon pattern, it may be represented that the situation of the analyte of the first time period is improved relative to the second time period. Thus, improvement in the situation of the analyte may be obtained intuitively.

In some examples, a reminder message may be created based on the improvement and output to a user, such as an object to be tested. For example, for an analyte that is glucose, the reminder message may be: "Compared to the last time, the dimensions of your current progress are: the first indicator, the second indicator, etc., continue to work hard to achieve the goals in an all-round way".

In some examples, the evaluation methods of the present disclosure may also process analyte data for multiple users, e. g. objects to be tested. That is, the processor of evaluation system 200 may also be configured to process analyte data for a plurality of users, e. g. objects to be tested.

In some examples, the evaluation method may also receive a plurality of analyte data from a plurality of objects to be tested during a predetermined time period to acquire a plurality of target polygon patterns. In some examples, an axis length corresponding to the same normalized analyte indicator for the target polygon patterns of the plurality of objects to be tested may be ranked. In this case, the ranking of each normalized analyte indicator may be used to increase the user's enthusiasm in improving the corresponding indicator. In some examples, a reminder message may be created based on ranking and output to a plurality of objects to be tested.

In some examples, after sorting the axial lengths corresponding to the same normalized analyte indicator of the target polygon patterns of a plurality of objects to be tested, the first several objects to be tested with the shortest axial length corresponding to each normalized analyte indicator may be selected, and a reminder message may be created and output to the first several objects to be tested. For example, if the corresponding analyte is glucose, the reminder message may be: "Your current short board is the first indicator, second indicator, etc., strive to improve these dimension indicators by 10% in the next cycle".

In some examples, a weighted average may be performed on a plurality of normalized analyte indicators of each object to be tested to acquire an average indicator value, and the average indicator values of each object to be tested is ranked. Thus, the user's enthusiasm for improving the situation of the analyte may be increased. In some examples, a reminder message may be created based on ranking and output to a plurality of objects to be tested. For example, if the corresponding analyte is glucose, the reminder message may be: "Your current glucose comprehensive ranking has defeated 10% of users". In some examples, objects to be tested that are ranked in the first several positions may be rewarded. Thus, the user's enthusiasm for improving the situation of the analyte may be effectively promoted.

Evaluation system 200 of the present disclosure acquires a plurality of analyte indicators based on analyte data of different time periods, the plurality of analyte indicators are normalized to acquire a plurality of normalized analyte indicators within a predetermined range, a plurality of polygon patterns for different time periods are acquired based on the corresponding normalized analyte indicators of different time periods, the polygon patterns of one of the time periods are evaluated by the polygon patterns of the different time periods, and the situation of the analyte may be obtained intuitively with respect to the analyte indicators. Thus, the readability of the analyte indicator may be improved.

Various embodiments of the disclosure may have one or more of the following effects. In some embodiments, the disclosure may provide an evaluation system based on analyte data with an improved readability of analyte indicators.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The invention claimed is:

1. An evaluation system based on analyte data, comprising a memory storing a program, a display, and a processor coupled with the memory and the display, wherein the processor is configured to:

receive analyte data during a predetermined time period from an object to be tested, wherein,
   the analyte data comprises a concentration of an analyte over time in the predetermined time period of the object to be tested, and
   the predetermined time period comprises a first time period and a second time period;
acquire a plurality of analyte indicators different from each other based on the analyte data;
normalize the plurality of analyte indicators to a predetermined range to acquire a plurality of normalized analyte indicators within the predetermined range;
plot a polygon pattern corresponding to the analyte data during the first time period as a target polygon pattern based on the plurality of normalized analyte indicators during the first time period;
plot a polygon pattern corresponding to the analyte data during the second time period as a reference polygon pattern based on the plurality of normalized analyte indicators during the second time period;
take a line segment between a vertex and a center point as an axis, the length of the axis reflecting each normalized analyte indicator and the center point of the target polygon pattern coinciding with the center point of the reference polygon pattern;
display the target polygon pattern and the reference polygon pattern, by the display, to evaluate the target polygon pattern;
to receive a plurality of analyte data during a predetermined time period from a plurality of objects to be tested to acquire a plurality of target polygon patterns and to rank the axis lengths corresponding to the same normalized analyte indicator in the target polygon patterns of the plurality of objects to be tested; and
create a reminder message based on the ranking and to output the reminder message to the plurality of objects to be tested;
wherein:
   the plurality of analyte indicators comprise a first indicator; and
   the first indicator is a ratio of an area under a straight line corresponding to a lower limit of a target analyte of an analyte curve corresponding to a lower decile to an area bounded by the analyte curve corresponding to upper deciles and the analyte curve corresponding to the lower deciles.

2. The evaluation system of claim 1, wherein, in at least one of the target polygon pattern and the reference polygon pattern, angles formed between axes are adjacent to each other are substantially the same.

3. The evaluation system of claim 1, wherein, for the same normalized analyte indicator, the axis of the target polygon pattern corresponding to the normalized analyte indicator is collinear with the axis of the reference polygon pattern corresponding to the normalized analyte indicator.

4. The evaluation system of claim 1, wherein:
the first time period is not less than 1 day;
the second time period is not less than 1 day; and
the length of the first time period is the same as the length of the second time period.

5. The evaluation system of claim 1, wherein:
the processor is further configured to plot a polygon pattern as a standard polygon pattern based on the predetermined range and the number of the plurality of analyte indicators;
the length of each axis reflects the range value of the predetermined range;

the center point of the standard polygon pattern coincides with the center point of the target polygon pattern; and for the same normalized analyte indicator, the axis of the standard polygon pattern corresponding to the normalized analyte indicator is collinear with the axis of the target polygon pattern corresponding to the normalized analyte indicator.

6. The evaluation system of claim 5, wherein the processor is further configured to:

take a point on an axis of the standard polygon pattern as a vertex and taking a center point of the standard polygon pattern as a center point; and plot a polygon pattern as an intermediate polygon pattern in a manner similar to the standard polygon pattern.

7. The evaluation system of claim 6, wherein the intermediate polygon pattern is lighter in color than the target polygon pattern.

8. The evaluation system of claim 1, wherein:

if the closer to the center point in the target polygon pattern represents the worse the analyte indicator is, the larger the area of the target polygon pattern represents the better the analyte is; and if the closer to the center point in the target polygon pattern represents the better the analyte indicator is, the smaller the area of the target polygon pattern represents the better the analyte is.

9. The evaluation system of claim 1, wherein, in at least one of the target polygon pattern and the reference polygon pattern:

scales are drawn for axes at different predetermined intervals; and each predetermined interval increases or decreases from the center point to the vertex.

10. The evaluation system of claim 9, wherein each of the predetermined intervals increases proportionally or differentially along a direction in which better analyte indicators are indicated in at least one of the target polygon pattern and the reference polygon pattern.

11. The evaluation system of claim 1, wherein:

the analyte is glucose;

the plurality of analyte indicators comprise the first indicator, a second indicator, and a third indicator;

the first indicator reflects a risk of low glucose;

the second indicator reflects a compliance rate of glucose during a corresponding time period; and the third indicator corresponding to average glucose.

12. The evaluation system of claim 11, wherein:

the plurality of analyte indicators further comprise a fourth indicator and a fifth indicator;

the fourth indicator reflects overall level and fluctuations of glucose; and the fifth indicator reflects the rate of change of average glucose.

13. The evaluation system of claim 12, wherein:

the plurality of analyte indicators further comprise a sixth indicator, a seventh indicator, and an eighth indicator;

the sixth indicator reflects glucose fluctuations due to physiological factors;

the seventh indicator reflects glucose fluctuations due to user behavior; and the eighth indicator reflects a risk of high glucose.

14. The evaluation system of claim 13, wherein:

the processor is configured to perform a weighted average on the normalized first indicator, the second indicator, the third indicator, the fourth indicator, the fifth indicator, the sixth indicator, the seventh indicator, and the eighth indicator to acquire an average indicator value;

the processor is configured to evaluate a situation of the analyte based on the average indicator value; and weights of the first indicator, the second indicator, the third indicator, the fourth indicator, the fifth indicator, the sixth indicator, the seventh indicator, and the eighth indicator decrease successively.

15. The evaluation system of claim 1, wherein:

in the target polygon pattern, a part between the boundary and the center point of the target polygon pattern is filled with a gradient color;

in the reference polygon pattern, a part between the boundary and the center point of the reference polygon pattern is filled with a gradient color; and a standard polygon pattern is lighter in color than the target polygon pattern.

16. The evaluation system of claim 1, wherein the predetermined range is 0 to 10.

17. The evaluation system of claim 1, wherein at least one of the target polygon pattern and the reference polygon pattern is a triangle, a quadrilateral, a pentagon, a hexagon, a heptagon, an octagon, or a nonagon.

* * * * *